United States Patent [19]
Killick et al.

[11] Patent Number: 5,631,205
[45] Date of Patent: May 20, 1997

[54] HERBICIDE, CROP DESICCANT AND DEFOLLIANT ADJUVANTS COMPRISING AN UNSATURATED FATTY ACID ETHYL ESTER AND A NON-IONIC EMULSIFIER

[75] Inventors: Robert W. Killick, Mt Waverley; Peter R. Wrigley, Blackburn South; Peter W. Jones, Box Hill South, all of Australia; David T. Schulteis, Fresno, Calif.

[73] Assignees: Victorian Chemical International Pty. Ltd., Richmond, Australia; Wilbur-Ellis Company, Fresno, Calif.

[21] Appl. No.: 545,665

[22] PCT Filed: May 5, 1994

[86] PCT No.: PCT/AU94/00229

§ 371 Date: Apr. 26, 1996

§ 102(e) Date: Apr. 26, 1996

[87] PCT Pub. No.: WO94/24858

PCT Pub. Date: Nov. 10, 1994

[30] Foreign Application Priority Data

May 5, 1993 [AU] Australia ................. PL8660

[51] Int. Cl.⁶ .................................................. A01N 25/30
[52] U.S. Cl. ...................... 504/116; 504/162; 252/356
[58] Field of Search ......................... 504/116, 162, 504/166, 167, 168, 170, 213, 214, 215, 253; 252/356

[56] References Cited

U.S. PATENT DOCUMENTS

| | | | |
|---|---|---|---|
| 2,626,862 | 1/1953 | Zimmerman et al. | 71/2.7 |
| 3,619,168 | 11/1971 | Mecklenborg | 71/106 |
| 3,620,712 | 11/1971 | Conklin et al. | 71/106 |
| 4,966,728 | 10/1990 | Hazen | 252/354 |
| 4,975,110 | 12/1990 | Puritch et al. | 71/113 |
| 5,035,741 | 7/1991 | Puritch et al. | 71/113 |
| 5,098,467 | 3/1992 | Puritch et al. | 71/113 |
| 5,098,468 | 3/1992 | Puritch et al. | 71/113 |
| 5,102,442 | 4/1992 | Hazen et al. | 71/91 |
| 5,106,410 | 4/1992 | Puritch et al. | 71/113 |
| 5,238,604 | 8/1993 | Hazen et al. | 252/356 |
| 5,284,819 | 2/1994 | Zorner et al. | 504/127 |
| 5,466,659 | 11/1995 | Keeney et al. | 504/130 |

FOREIGN PATENT DOCUMENTS

| | | |
|---|---|---|
| 40236/89 | 3/1990 | Australia . |
| 53806/90 | 11/1990 | Australia . |

*Primary Examiner*—S. Mark Clardy
*Attorney, Agent, or Firm*—Seidel, Gonda, Lavorgna & Monaco, PC

[57] ABSTRACT

An adjuvant composition for use with a herbicide, crop desiccant, or defoliant consisting essentially of an ethyl ester of a fatty acid with an unsaturation level of at least 40% and a non-ionic ionic emulsifier.

18 Claims, No Drawings

HERBICIDE, CROP DESICCANT AND DEFOLLIANT ADJUVANTS COMPRISING AN UNSATURATED FATTY ACID ETHYL ESTER AND A NON-IONIC EMULSIFIER

This application has been filed under 35 USC 371 from international application PCT/AU 94/00229 filed May 5, 1994.

FIELD OF THE INVENTION

This invention relates to compositions that are used as adjuvants to facilitate the effectiveness of herbicides, crop desiccants and defoliants. More particularly such compositions have proved most effective against post-emergent weeds during the growing of corn and soyabean crops, the desiccation of potato and alfalfa foliage and the defoliation of cotton leaves.

BACKGROUND OF THE INVENTION

To maximise crop yields it has become essential to eliminate competing growths to allow the specific crops to grow unhindered. To this end the chemical industry has developed a range of herbicides to combat almost every weed. Similarly to facilitate mechanical harvesting it has been found necessary to either desiccate the foliage of potatoes and alfalfa or defoliate the cotton leaves before the cotton is plucked.

The man on the land knows however that no herbicide gives a complete strike rate so a burgeoning sub-industry has developed by which the efficacy of herbicides can be improved. Many names have been used to describe such compounds including "suffactants", "spreaders", "crop oil concentrates" and "spray adjuvants".

To overcome the problem in general for the industry and in particular for its own herbicides the BASF organisation patented systems in 1989 (U.S. Pat. No. 4,834,908 "Antagonism Defeating Crop Oil Concentrates" and Australian Patent 625194 "Adjuvants for use with Crop Protection Agents"). These systems are based on a concentrate comprising in essence 20–90% of a fatty acid ester, 4–40% of an anionic surfactant selected from the partial sulphate and phosphate esters of ethoxylates and from 7–20% of a fatty acid. A 100 parts of this blend is added to 140 parts of a hydrocarbon.

In the field, the system has been by-passed by the use of the simple methyl fatty esters emulsified with suffactants.

Another approach has been disclosed in an article entitled "Small Grass and Grass Weed Response to BAS-514 with Adjuvants" (Manthey et al) in Volume 4 Issue 2 of Weed Technology. The use of methyl, ethyl and butyl estefified sunflower oil is discussed as adjuvants for BAS-514. This study showed enhancing of BAS-514 by their use. There was no noted significant difference in efficacy between methyl, ethyl and butyl esters.

It is recognised that even these products are not optimising the efficacy of the herbicides.

To facilitate the gathering of potatoes and alfalfa seed, current practice is to desiccate the growing plants' foliage before harvest. Certain cationic materials are recommended with products such as DES-I-CATE and DIQUAT HERBICIDE - HA being well known on the field. It has also been found that their effectiveness may be enhanced by use of adjuvants such as AD-IT which is based on emulsified methyl oleate.

Similar to the current adjuvants for herbicides neither the total effectiveness, nor the rate of the desiccation is completely satisfactory for the farmer.

While the mechanical harvesting of crops such as cotton, tomatoes and beans has lowered production costs, it has also created new problems. In the case of cotton, mechanical harvesting has created perplexing problems at gins and textile mills. Such mechanically harvested cotton absorbs moisture from the spindles of the harvester and contains considerably more than the normal 5 to 15 percent of trash present in hand-picked cotton. Particularly bothersome is leaf material which is one of the most difficult types of trash to remove. This additional moisture and trash in mechanically harvested cotton frequently complicates ginning operations and raises the costs of textile manufacturing by requiring additional steps in cleaning the cotton at the mill.

Recent efforts have been directed toward the development of various chemical treatments for the crop plant in an effort to overcome the objectionable attributes of mechanically harvested cotton. For example, processes have been suggested in recent years which have as their objective to provide increased yields of the desired crop and/or to inhibit rank growth. Such processes have been effective in some respects. However, some of the prior art methods require the use of expensive surfactants in order to obtain satisfactory application of the chemical product to the plant. Other prior art methods produce an insufficient increase in the crop yield and/or decreases in rank growth for economic utilisation.

As the answer to this need, a plant growth regulator and its method of use were patented in 1984 "Plant Growth Regulator and Method for the Use Thereof" (U.S. Pat. No. 4,439,224). Whilst significant improvement was achieved, decreased trash limits continue to be set by the mills demanding further improvements in the level of defoliation.

SUMMARY OF THE INVENTION

It has now been surprisingly found that certain blends enhance the activity of herbicides, crop desiccants and defoliants.

In a first embodiment of the invention, an adjuvant composition is provided for use with a herbicide, crop desiccant or defoliant including:
(i) one or more alkyl esters of fatty acids having a level of unsaturation of at least 40%; and
(ii) a non-ionic emulsifier.

The higher levels of unsaturated fatty acids are preferred being more effective as penetrants. Preferably the alkyl esters comprise at least 50% of the composition and are ethyl esters.

There are innumerable variations of the preferred ethyl ester since the ethyl esters of fatty acids may be produced from the natural oils and fats such as lard, tallow and vegetable oils or from specific blends produced by fatty acid manufacturers or from fatty acids produced by synthetic means. Readily available commercial vegetable oils such as canola, corn, sunflower and soyabean oils are also sources for fatty acids. Such fatty acids will generally be described in this patent specification as unsaturated fatty acids or oleates.

The non-ionic emulsifiers are well known to those skilled in the art, and it is recognised there are a multitude of combinations. Preferably a non-ionic ester of the fatty acid moiety provides unexpected emulsification and coupling effects to furnish a finished homogeneous product.

The ethyl esters and non-ionic emulsifier work in synergy firstly to provide the right emulsification characteristics of the alkyl esters and secondly to modify the surface properties of the plant foliage to maximise the ingress of the active ingredient, ie the herbicide, dessicant or defoliant.

In another preferred embodiment, the non-ionic emulsifiers are a combination of alkylaryl ethoxylate and a polyethyleneglycol (PEG) ester of fatty acids. Preferably, the alkylaryl ethoxylate is octyl, nonyl or dodecylphenol with 3 to 13 moles of ethylene oxide, whilst the PEG ester is of molecular weight range 200–600 with either one or two moles of unsaturated fatty acids.

Whilst it is acknowledged that the emulsifiers outlined above cover a wide range of physical properties and provide wide ranging emulsification abilities, it is important to note that a balance between two quite different emulsifiers can produce a far greater effect than an intermediate emulsifier. With this in mind, many combinations of alkylaryl ethoxylates and PEG esters can provide adequate emulsification of alkyl esters of unsaturated fatty acids for adjuvant systems. A preferred combination is ethoxylated nonylphenol with 9 moles of ethylene oxide and PEG 400 di-oleate in the ratio 1:2 by weight.

In another preferred embodiment, the non-ionic emulsifier is the ethoxylated soya-amine base. A preferred emulsifier would have 15 mole ethoxylation.

In other preferred embodiments, other non-ionic emulsifiers of interest are those based on the fatty alcohols. A preferred emulsifier would have 6 mole ethoxylation on the 12 carbon alcohol.

The adjuvant compositions are used to penetrate or soften the waxy protective layer of the plant's foliage. Several methods have been developed to determine an ingredient's penetrative, "softening" or solvent power. The most appropriate laboratory technique evolved by the petroleum oil industry is a method, called the Aniline Point, which is specifically used to determine the solvent power of cleaners, thinners, etc. From multitudinous studies, it is well known that as the molecular weight of a paraffin oil increases, the Aniline Point increases and the solvent power decreases. By way of example, set out below is information taken from "Exxon Chemical Performance Products for Pesticides".

|  | Paraffin Content | Molecular Weight (Avge) | Aniline Point (°C.) |
|---|---|---|---|
| Norpar 12 | 99.1 | 163 | 82 |
| Norpar 13 | 99.4 | 189 | 87 |
| Norpar 15 | 99.1 | 212 | 92 |

Similar results are seen with the alkyl esters of the unsaturated fatty acids, in this case the oleates from canola oil. Because of these products' solvent power the test undertaken is the Mixed Aniline Point.

|  | Molecular Weight (Avge) | Mixed Aniline Point (°C.) |
|---|---|---|
| Methyl Oleate | 296 | −8.4 |
| Ethyl Oleate | 310 | 0.0 |
| iso-Propyl Oleate | 324 | +5.4 |
| n-Butyl Oleate | 338 | +10.0 |

Based on these results, it would be expected that the most effective oil blend would be based on methyl oleate. Against this technical expectation, it has been surprisingly found that the preferred oil blend is based on the ethyl oleate as seen in the Examples.

EXAMPLES

The effectiveness of the compositions of the invention have been subject to a series of trials.

Product blends were made as follows:

|  | (% w/w) |
|---|---|
| Composition 1 | |
|  | HASTEN |
| Ethyl Oleate | 76 |
| PEG 400 di-oleate | 16 |
| Nonyl phenol ethoxylate (9EO) | 8 |
| Composition 2 | |
| EOD | VICCHEM |
| Ethyl Oleate | 80 |
| Soya-amine ethoxylate (15EO) | 20 |
| Composition 3 | |
| EOA | VICCHEM |
| Ethyl Oleate | 50 |
| Fatty alcohol ethyoxylate (12A6) | 40 |
| PEG 400 mono oleate | 10 |

Herbicides

The results shown in the Tables are the mean results from experiments conducted. The compositions were assessed against various weeds—velvet leaf, common lambs quarters, giant foxtail, pig weed, spring amaranth, ivy leaf, morning glory and prickly sida. Velvet leaf is of most concern to the farmer being the most difficult to control.

After the non-treated control, the proprietary adjuvants tested included X-77 (a simple surfactant of a non-ionic blend of a nonyl ethoxylate and oleic acid); CAYUSE the original water based product of a blend of ammonium sulphate and phosphate ester; CAYUSE PLUS designed to meet the herbicide manufacturer's nitrogen recommendation a blend of ammonium sulphate, ammonium nitrate and phosphate ester; SUN-IT II methylated seed oil (methyl oleate) with nonionic emulsifiers; and HASTEN with ethyl oleate as is shown in Composition 1.

TABLE 1

Herbicide: PURSUIT (25 gram/acre)
Visual Injury (%)
14 Days After Treatment

|  | Velvet leaf | Common Lamb Quarters | Giant Foxtail |
|---|---|---|---|
| Non Treated Control | 0 | 0 | 0 |
| X-77 (0.25%) | 41 | 45 | 46 |
| CAYUSE (1 pint/acre) | 67 | 44 | 68 |
| CAYUSE PLUS (2 pints/acre) | 70 | 38 | 78 |
| SUN-IT II + 28% N (2 pints/acre) | 73 | 45 | 81 |
| HASTEN + 28% N (2 pints/acre) | 84 | 49 | 83 |

TABLE 2

Herbicide: PURSUIT (25 gram/acre)
Visual Injury (%)
14 Days After Treatment

|  | Velvet leaf | Common Lamb Quarters | Giant Foxtail |
|---|---|---|---|
| Non Treated Control | 0 | 0 | 0 |
| CAYUSE PLUS (2 pints/acre) | 73 | 56 | 69 |

TABLE 2-continued

Herbicide: PURSUIT (25 gram/acre)
Visual Injury (%)
14 Days After Treatment

| | Velvet leaf | Common Lamb Quarters | Giant Foxtail |
|---|---|---|---|
| SUN-IT II (1.5 pints/acre) + 28% N (2 pints/acre) | 71 | 49 | 89 |
| HASTEN (1.5 pints/acre) + 28% N (2 pints/acre) | 83 | 68 | 100 |

TABLE 3

Herbicide: PURSUIT (25 gram/acre)
Visual Injury (%)
14 Days After Treatment

| | Velvet leaf | Common Lamb Quarters | Giant Foxtail |
|---|---|---|---|
| Non Treated Control | 0 | 0 | 0 |
| X-77 (0.25%) | 41 | 56 | 61 |
| CAYUSE (1 pint/acre) | 74 | 61 | 81 |
| CAYUSE PLUS (2 pints/acre) | 70 | 43 | 74 |
| SUN-IT II (2 pints/acre) + 28% N (2 pints/acre) | 81 | 71 | 90 |
| HASTEN (2 pints/acre) + 28% N (2 pints/acre) | 84 | 69 | 80 |

TABLE 4

Herbicide: PURSUIT (4 ozs/acre)
All Visual Injury (%)
10 Days After Treatment

| | Velvet leaf | Pigweed | Spring Amath |
|---|---|---|---|
| Non Treated Control | 0 | 0 | 0 |
| CAYUSE (1 pint/acre) | 36.3 | 81.3 | 96.5 |
| CAYUSE PLUS (2 pints/acre) | 31.3 | 77.5 | 96.5 |
| HASTEN (2 pints/acre) + 28% N (2 pints/acre) | 51.3 | 85.8 | 99.5 |

TABLE 5

Herbicide: CLASSIC/PINNACLE (0.25 oz/0.25 oz/acre)
All Visual Injury (%)
10 Days After Treatment

| | Velvet leaf | Pigweed | Prickly Sida |
|---|---|---|---|
| Non Treated Control | 0 | 0 | 0 |
| CAYUSE (0.5 pints/acre) | 37.5 | 90.0 | 2.5 |
| CAYUSE PLUS (1 pint/acre) | 52.5 | 86.3 | 11.3 |
| HASTEN (½ pints/acre) + 28% (1 pint/acre) | 50 | 83.8 | 12.5 |

TABLE 6

Herbicide: BEACON (0.76 oz/acre on corn crops)
All Visual Injury (%)
26 Days After Treatment

| | Velvet leaf | Ivy leaf/ Morning Glory | Giant Foxtail |
|---|---|---|---|
| SUPERB (methylated seed oil) (1 qt/acre) | 88 | 65 | 80 |
| HASTEN (1 qt/acre) | 93 | 85 | 85 |

TABLE 7

Herbicide: PURSUIT (4 oz/acre on soybean crops)
All Visual Injury (%)
26 Days After Treatment

| | Velvet leaf | Ivy Leaf Morning Glory | Giant Foxtail |
|---|---|---|---|
| SUN-IT (1.5 pints/acre) | 75 | 80 | 83 |
| HASTEN (2 pints/acre) | 77 | 90 | 85 |

TABLE 8

Herbicide: ACCENT (0.023 pound active ingredient/acre)
All Visual Injury (%)
21 Days After Treatment

| | ECHCG | SETLU | SETVI | SETFA |
|---|---|---|---|---|
| No adjuvant | 10 | 73 | 70 | 50 |
| SUN-IT (1 quart/acre) | 67 | 87 | 88 | 85 |
| HASTEN (1 quart/acre) | 93 | 80 | 80 | 90 |

ECHCG = Barn yard grass
SETLU = Yellow foxtail
SETVI = Green foxtail
SETFA = Giant foxtail All the test results in Tables 1 to 8 (inclusive) show that the HASTEN composition caused the greatest percentage visual injury with a variety of weeds tested and in conjunction with a variety of commercially available herbicides.

Desiccants

To facilitate the gathering of potatoes and alfalfa seed for example, current practice is to desiccate the growing plants' foliage before harvest. Certain cationic materials are recommended with products such as DES-I-CATE and DIQUAT HERBICIDE - H/A being well known on the field.

Potato foliage was sprayed 10 to 14 days prior to harvest with, for ground application, about 600 ml per acre for DIQUAT HERBICIDE and around 9.6 litres per acre for DES-I-CATE in 96 to 480 litres of total spray.

To improve the efficacy of these desiccants AD-IT [a proprietary product from the Wilbur Ellis Company] was added to the solution to provide 9.6 litres of AD-IT adjuvant per acre. AD-IT is a blend of methyl oleate and a mixture of nonionic emulsifiers.

A trial was conducted comparing this material against a composition known as VICCHEM EOD (see Composition 2) at the same usage rates noted above. Visual rating was undertaken at 10 and 14 days. See Table 9.

TABLE 9

| | Visual Injury | |
|---|---|---|
| | 10 days | 14 days |
| AD-IT | average | average |
| VICCHEM EOD | superior | above average |

Defoliants

The traditional and still widely used method of defoliation of cotton uses sodium chlorate with or without the cationic PARAQUAT. In newer techniques specific defoliants such as DROPP, (thidiazuron, a substituted urea) and the organo phosphate FOLEX are used. At the time these defoliants are sprayed onto the cotton bushes several ingredients are incorporated in the spray solution. These include PREP (a boll opener), BIVERT, (a drift control and depostition retention agent), MOR-ACT (a crop oil concentrate based on petroleum oil and surfactants), SYLGARD 309 (an organo silicon surfactant), TRISERT CB (an organo nitrogen product providing 26% Nitrogen) and R-11 (a proprietary non-ionic suffactant). HASTEN is that shown in Composition 1.

Defoliation figures show the leaves that have fallen from the plant. Desiccation shows the level of leaves still on the plant but expected to fall soon. The open bolls show the cotton pods which are open and ready to be picked.

The first set of trials were undertaken in Shafter County, Calif. All treatments were applied at 20 gallons/acre by ground spray and results were assessed after 9 days. See Table 10.

TABLE 10

| Treatment | #1 | #2 | #3 | #4 | #5 | #6 |
|---|---|---|---|---|---|---|
| DROPP (lbs/acre) | 0.2 | 0.2 | 0.2 | 0.2 | 0.2 | 0.2 |
| PREP (qt/acre) | 1 | 1 | 1 | 1 | 1 | 1 |
| BIVERT (pt/acre) | 0.75 | 0.75 | 0.75 | 0.75 | 0.75 | 0.75 |
| MOR-ACT (pt/acre) | 1 | | | 1 | | |
| SYLGARD (pts/100 gall) | | 2 | 4 | | 2 | 4 |
| TRISERT (gal/100 gal) | | | | 1 | | |
| HASTEN (pints/100 gal) | | | | | 4 | 8 |
| Defoliation (%) | 58.9 | 50.9 | 68.9 | 71.4 | 80.9 | 83.6 |
| Desiccation (%) | 0.7 | 1.0 | 1.0 | 7.5 | 2.6 | 10.0 |
| Open bolls (%) | 84.0 | 86.8 | 91.5 | 89.0 | 94.9 | 94.6 |

A second set of trims were undertaken in Fresno County, Calif. All trials were applied at 30 gallons/acre by ground spray and results were assessed after 11 days. This was an extreme trial as the cotton plants had excess vegetation from over-fertilisation and watering. See Table 11.

TABLE 11

| Treatment | #1 | #2 | #3 | #4 | #5 |
|---|---|---|---|---|---|
| FOLEX (pints/acre) | 3 | 3 | 3 | 3 | 3 |
| PREP (pints/acre) | 2 | 2 | 2 | 2 | 2 |
| BIVERT (pint/acre) | 1 | 1 | 1 | 1 | 1 |
| MOR-ACT (pint/acre) | 1 | | | 1 | 1 |
| SYLGARD (pints/acre) | | 4 | 4 | | |
| TRISERT (gal/100 gal) | | | | 1 | 4 |
| HASTEN (pints/100 gal) | | | 8 | | 4 |
| Defoliation (%) | 37.9 | 49.4 | 55.4 | 51.5 | 47.1 |
| Desiccation (%) | 14.5 | 30.7 | 45.9 | 47.2 | 29.5 |
| Open bolls (%) | 47.7 | 57.8 | 70.0 | 54.8 | 64.8 |

The third set of trials were again undertaken in Fresno County, Calif. All trials were applied at 20 gallons/acre by ground spray and results were assessed after 7 days. See Table 12.

TABLE 12

| Treatment | #1 | #2 | #3 | #4 | #5 |
|---|---|---|---|---|---|
| FOLEX (pints/acre) | 2 | 2 | 2 | 2 | 2 |
| PREP (pints/acre) | 2 | 2 | 2 | 2 | 2 |
| BIVERT (pints/acre) | 0.5 | 0.5 | 0.5 | 0.5 | 0.5 |
| R-11 (pints/100 gal) | 2 | | | | |
| SYLGARD (pints/100 gal) | | 2 | 2 | 4 | 4 |
| HASTEN (pints/100 gal) | | | 4 | | 8 |
| Defoliation (%) | 87.5 | 77.6 | 87.3 | 83.4 | 89.1 |
| Desiccation (%) | 23.3 | 6.5 | 9.8 | 13.2 | 21.2 |
| Open bolls (%) | 77.4 | 70.4 | 69.6 | 76.5 | 68.3 |

A major field trial was conducted at the K5 cotton field at "The Gardens" Wee Waa Australia. The field was divided into two 33 hectare blocks East and West. The western side was treated with the following formulation.

| D C Tron Oil | 2 liters/ha |
|---|---|
| DROPP | 100 gm/ha |
| Dimethoate | 500 ml/ha |

D C Tron Oil is an emulsified paraffinic petroleum oil and is used throughout the district.

The product was applied by aerial spray at a water volume of 20 litre/hectare. The temperature was 20° C., humidity 75% and wind at a 5 knot northerly.

For the eastern side HASTEN (see Composition 1) was directly substituted for D C Tron Oil at the same volume.

Significant leaf defoliation differences were observed as follows where senesced leaf is classified as a leaf which fails from the plant when flicked with the finger. See Table 13.

TABLE 13

| | East-HASTEN | | West-D C Tron | |
|---|---|---|---|---|
| | Green Leaf | Senesced Leaf | Green Leaf | Senesced Leaf |
| Pre-Spray | 135 | 12 | 165 | 14 |
| 5 days | 4 | 19 | 26 | 35 |
| 9 days | 2 | 5 | 12 | 10 |
| 12 days | 0 | 3 | 6 | 6 |
| | Percentage of Green Leaves Remaining | | | |
| 5 days | 3% | | 16% | |
| 9 days | 1% | | 7% | |
| 12 days | 0% | | 4% | |

It was observed that green leaf drop was faster and more complete in the eastern side (ie. treated with HASTEN). This was particularly obvious in the 5 day assessment.

Consequently as the defoliation was relatively quick, picking can commence earlier and also achieve better grades of cotton through the absence of foliage.

We claim:

1. An adjuvant composition consisting essentially of
    (i) an ethyl ester of a fatty acid wherein the ethyl ester has a level of unsaturation of at least 40% by weight; and
    (ii) a non-ionic emulsifier.

2. A composition according to claim 1 wherein the ethyl ester comprises at least 50% by weight of the total composition.

3. A composition according to claim 1 wherein the non-ionic emulsifier is a combination of two or more non-ionic emulsifiers.

4. A composition according to claim 1 wherein the non-ionic emulsifier is a polyethyleneglycol (PEG) ester of fatty acids.

5. A composition according to claim 4 wherein the non-ionic emulsifier is a polyethyleneglycol (PEG) with a molecular weight range of 200–600 esterified with either one or two moles of unsaturated fatty acids.

6. A composition according to claim 1 wherein the non-ionic emulsifier is of the alkylarylethoxylate type.

7. A composition according to claim 6 wherein the alkylarylethoxylate is octyl-, nonyl- or dodecylphenol with 3 to 13 moles of ethylene oxide.

8. A composition according to claim 1 wherein the non-ionic emulsifier is a combination of an alkylarylethoxylate and a polyethyleneglycol (PEG) ester of unsaturated fatty acids.

9. A composition according to claim 8 wherein the non-ionic emulsifier is ethoxylated nonylphenol with 9 moles of ethylene oxide and PEG 400 di ester of unsaturated fatty acids in the ratio 1:2 by weight.

10. A composition according to claim 9 wherein the unsaturated fatty acids are based on oleine.

11. A composition according to claim 1 wherein the non-ionic emulsifier is ethoxylated soy-amine base.

12. A composition according to claim 11 wherein the non-ionic emulsifier has 15 mole ethoxylation.

13. A composition according to claim 1 wherein the non-ionic emulsifier is of the fatty alcohol ethoxylate type.

14. A composition according to claim 13 wherein the non-ionic emulsifier has 6 mole ethoxylated on the 12 carbon fatty alcohol.

15. A herbicide composition consisting essentially of:
(i) a herbicide; and
(ii) an amount of an adjuvant composition according to claim 1, which is at least an equal weight of the active level of the herbicide.

16. A crop desiccant composition consisting essentially of:
(i) a crop desiccant; and
(ii) an amount of an adjuvant composition according to claim 1, which is at least an equal weight of the active level of the desiccant.

17. A defoliant composition consisting essentially of:
(i) a defoliant; and
(ii) an amount of an adjuvant composition according to claim 1, which is at least an equal weight of the active level of the defoliant.

18. An agricultural chemical composition comprising:
(i) an agricultural chemical; and
(ii) an amount of an adjuvant composition according to claim 1, which is at least an equal weight of the active level of the agricultural chemical.

* * * * *